United States Patent [19]
Haider

[11] Patent Number: 5,782,833
[45] Date of Patent: Jul. 21, 1998

[54] PEDICLE SCREW SYSTEM FOR OSTEOSYNTHESIS

[76] Inventor: Thomas T. Haider, 2357 Knob Hill Dr., Riverside, Calif. 92506

[21] Appl. No.: 771,133

[22] Filed: Dec. 20, 1996

[51] Int. Cl.$^6$ ................................................. A61B 17/70
[52] U.S. Cl. ............................................ 606/61; 606/73
[58] Field of Search ........................... 606/60, 61, 72, 606/73

[56] References Cited

U.S. PATENT DOCUMENTS

| | | | |
|---|---|---|---|
| 5,005,562 | 4/1991 | Cotrel | 606/61 |
| 5,092,867 | 3/1992 | Harms et al. | 606/61 |
| 5,129,388 | 7/1992 | Vignaud et al. | 606/61 |
| 5,154,719 | 10/1992 | Cotrel | 606/73 |
| 5,176,678 | 1/1993 | Tsou | 606/61 |
| 5,176,680 | 1/1993 | Vignaud et al. | 606/61 |
| 5,190,543 | 3/1993 | Schläpfer | 606/61 |
| 5,217,497 | 6/1993 | Mehdian | 623/17 |
| 5,261,907 | 11/1993 | Vignaud et al. | 606/60 |
| 5,344,422 | 9/1994 | Frigg | 606/61 |
| 5,360,431 | 11/1994 | Puno et al. | 606/72 |
| 5,385,583 | 1/1995 | Cotrel | 623/17 |
| 5,443,467 | 8/1995 | Biedermann et al. | 606/65 |

OTHER PUBLICATIONS

Moss–Miami 3 Dimensional Spinal Instrumentation by Depuy Motech, Inc.—1993—advertising brochure.
Silhouette Spinal System, Spinal Innovations, Inc., 1996 advertising brochure.

*Primary Examiner*—Michael Buiz
*Assistant Examiner*—David O. Reip
*Attorney, Agent, or Firm*—Harold L. Jackson

[57] ABSTRACT

A pedicle screw assembly 10 for use with a rod 11 for the immobilization of bone segments. The assembly is composed of a screw 12, a polyaxial housing 20, a washer 34, a set screw 48, and a cup-shaped cap 40. When the screw is placed inside the polyaxial housing 20, the head of the screw 18 comes into contact with a middle section of the polyaxial housing 20 and is secured into the bone so that the polyaxial housing is pivotable with three degrees of freedom. The housing includes a pair of upstanding posts 30 with interior threads. A washer 34 is inserted between the head of the screw 12 and the rod. A cap 40, having a bottom, with a pair of posts accommodating openings 43 and a lateral cross connector 44, is placed over the posts 30 so that the cross connection 44 engages the rod. A set screw 48 is threaded into the housing posts to secure the rod within the housing.

5 Claims, 2 Drawing Sheets

५,७८२,८३३

PEDICLE SCREW SYSTEM FOR OSTEOSYNTHESIS

BACKGROUND OF THE INVENTION

1. Field of the Invention

The present invention relates to the medical field commonly referred to as Osteosynthesis, i.e., the fusion between segments of the spine and more particularly to a pedicle screw and rod system for immobilizing the segments during the fusion process.

2. Description of the Prior Art

Osteosynthesis is achieved by immobilizing the bone. When trying to achieve osteosynthesis and specifically fusion between different segments of the spine, one has to provide some type of immobilization. There are various prior art systems which try to achieve this purpose. The different systems involve placement of screws into the bone. The screws are then connected to each other by use of various sizes of rods or a plate. The bone segments that are being connected, especially in the spine, may be carrying different angles and different medical-lateral positions. Placement of a rod with a rigid screw or placement of a plate between two rigid screws is difficult because of the medial lateral displacement or angulation at different segments. One has to bend the rod or plate and at times achieve a complex bend in order to connect two different segments of the bone and especially two different areas in the spine. When dealing with the spine, the screws are ordinarily placed into the pedicle, and due to the different positions of the pedicle and different angulations of the screw as it enters the pedicle, one encounters difficulty in positioning and connecting these screws at various points.

Even though one can create a complex bend at the rod or the plate in order to connect two or more screws, there are places in the pedicle where one runs the chance of stress risers at different points and breakage of the system as the bends can never be perfect.

A screw system, which is capable of accommodating the rod in a perfect location without creating any appreciable areas of stress riser, will alleviate some of the above problems. Such a screw system would allow the rod to be bent to achieve fixation between two different points while adjusting to any imperfections in the bend.

There is at least one polyaxial screw system that has been used in the past which will achieve some of these goals; however, there are some inherent problems with this particular system. This polyaxial screw has many components which makes placement of such a screw cumbersome, which in turn, lengthens the operative time for this particular procedure. The system has a locking screw on the inside as well as a locking nut on the outside of the housing, which causes the operation to take much longer to perform. The fixation point which will lock the polyaxial screw and keep it from angling once the system is tightened is also not ideal.

Several patents teach the use of a pedicle screw system which appear to provide several degrees of freedom (i.e., rotation and limited angular deflection about a fixed point) for the immobilization of bone segments. See for example U.S. Pat. No. 5,360,431 to Puno et al and U.S. Pat. No. 5,176,678 to Tsou. Each of these patented structures has certain drawbacks including the use of a conventional nut to secure the rod into place for support of the bone segments. The nuts have flat surrounding edges which are engaged by a wrench to tighten the nut. Due to the surrounding tissue, and the confined area, difficulty can arise in placing the nut in the correct position thus requiring even more time to perform the operation. During the operation the patient is under anesthesia and this extra time increases the risk to the patient. Also, when secured the nut protrudes into the surrounding soft tissue after the operation is completed. This protrusion can lead to irritation of the surrounding soft tissue and possibly inflammation.

Another problem arising with the use of the nut is the tightening process. The nut is secured through the use of a wrench. The wrench requires space around the nut to be operable which necessarily increases the scope of the surgical procedure. Furthermore, the wrench should not come into contact with the surrounding soft tissue to avoid the possibility of peripheral tissue damage. These limitations tend to further increase the risk to the patient during the operation.

Yet another issue is the stability of the apparatus once in place. The tightening of the nut secures the screw, rod, and remaining elements of the assembly into place. In this application, only a minimal amount of the surface area of the top of the head of the screw is engaged for securing. An optimal securing of the apparatus would involve utilizing more of the surface area of the head of the screw.

There is a need for a more reliable pedicle screw and rod system which may readily and rapidly be secured in place, with less bulky equipment and which is less intrusive to the surrounding soft tissue.

SUMMARY OF THE INVENTION

The present invention addresses the stabilization of bone segments through the use of a polyaxial pedicle screw assembly and rod. The rod is arranged to be secured between two or more embedded screw assemblies to immobilize segments of the spine. The assembly is secured in place by tightening a screw, having a head and a threaded cylindrical shaft, into the bone. The head of the screw has a top and bottom, both of which are spherically convex in shape with the head being larger than the diameter of the cylindrical shaft. The top of the screw head has a wrench engaging surface, such as an allen wrench socket.

The screw fits within a polyaxial housing having a stepped bore adapted to receive the rod. The polyaxial housing is divided into three sections. The top section of the housing receives the entire screw including the head and is formed by a pair of spaced upstanding posts which define a U-shaped slot therebetween for receiving the rod. The inner walls of the posts are threaded for receiving a set screw which secures the rod in place. The middle section of the housing has an inner spherically concave surface for cradling the bottom of the head of the screw. The bore through the bottom section has a diameter which allows only the threaded cylindrical shaft to pass through. The screw, after insertion into the polyaxial housing, is threadably secured into the bone.

After the screw and housing are in place, the rod may be inserted within the U-shaped slot to rest on the top of the head of the screw. It is preferable, however, to insert a washer between the screw head and the rod.

Such a washer is placed within the upper section of the housing and is provided with a spherically concave bottom surface to cover the head of the screw. The top of the washer has a longitudinal saddle shape which conforms to the shape of the rod.

The washer, while optional, provides for an increased frictional surface area between the rod and the screw head and thereby adds to the stability of the rod and screw, once in place.

The screw assembly further includes a cup-shaped cap having two opposing openings to receive the posts and a cross-connector extending across the bottom of the cap. The cross-connector has a flat top and a bottom with a longitudinal saddle shape to conform to the shape of the rod. The cup-shaped cap is adapted to be placed over the polyaxial housing with the bottom surface of the cross-connector making contact with the rod.

A set screw of conventional configuration is arranged to be threaded into the top section of the polyaxial housing by means of a wrench inserted into a wrench engaging surface, such as a allen wrench socket, in the top of the set screw, to tighten the assembly into place.

With the set screw in place, but not tightened, the assembly has three degrees of freedom, i.e., rotatable and angularly positionable about the head of the screw. The tightening of the set screw secures the assembly into a single position. The set screw allows the assembly to be tightened while overcoming the disadvantage of potential soft tissue damage due to the use of a nut. The screw assembly of the present invention when secured in place does not protrude into the surrounding soft tissue and thus reduces the risk of irritation and soft tissue damage.

The present invention provides a highly flexible bone segment immobilization system with a minimum number of components which results in a reduction in the time that a patient must remain under anesthesia.

The construction and operational features of the present invention may best be understood by reference to the following description taken in conjunction with the appended drawings in which like components in the several figures are identified by the same reference numerals.

DESCRIPTION OF THE PREFERRED EMBODIMENT

Figure 1:
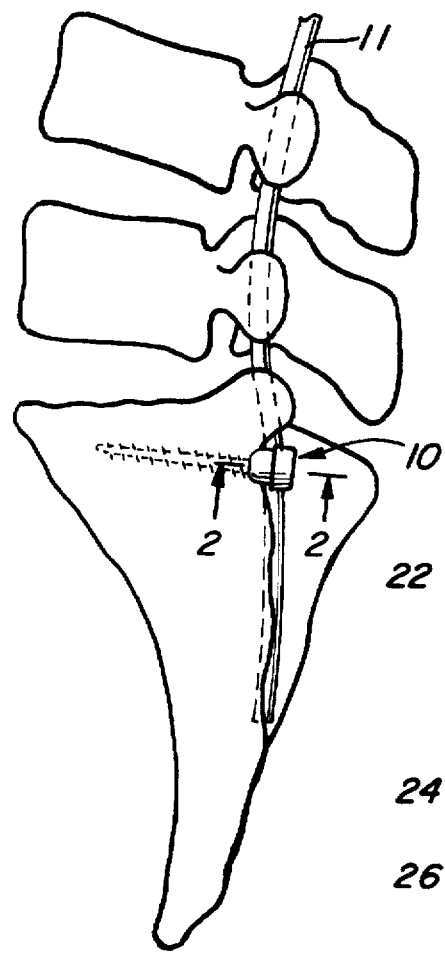
FIG. 1 is a diagrammatic view of several segments of a spiral column with a pedicle screw assembly and rod, in accordance with the present invention, secured thereto.

Referring now to the drawings and particularly to FIG. 1, a pedicle screw assembly 10, in accordance with the present invention, is intended to be secured in bone segments of a patient's spine and in conjunction with a rigid (though bendable) rod 11, to immobilize and allow the segments to fuse together.

Figure 2:
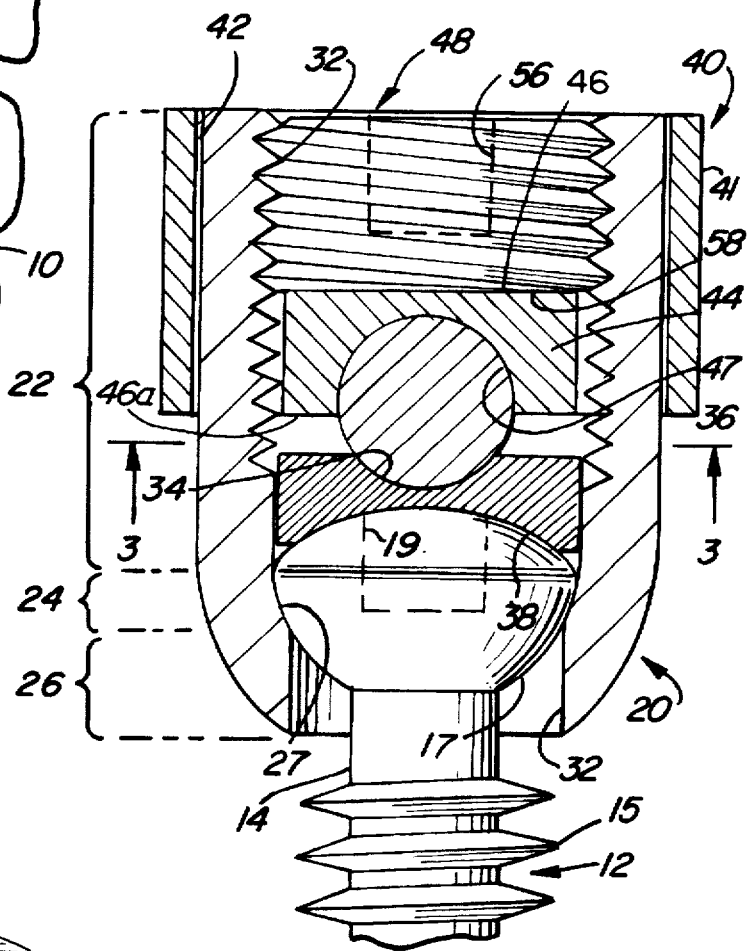
FIG. 2. is a cross-sectional view of the assembled pedicle screw assembly taken along lines 1—1 of FIG. 1, showing only a portion of the screw shaft.
Figure 3:
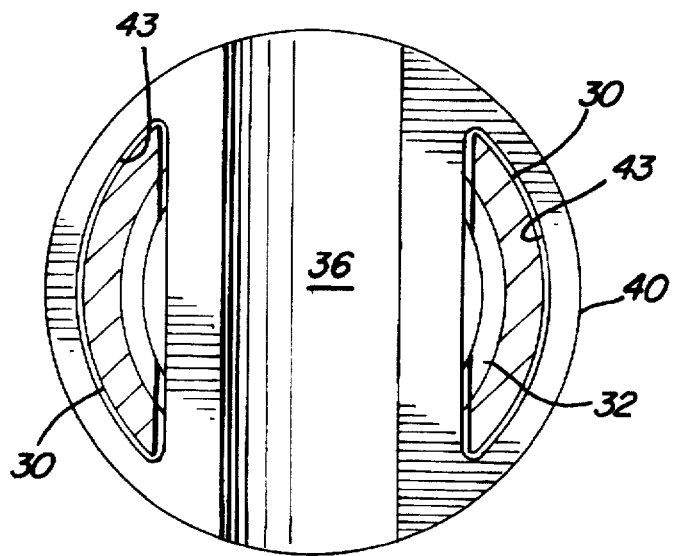
FIG. 3 is a cross-sectional view of the assembly taken along lines 3—3 of FIG. 2, showing the top of the washer, the housing posts and the lower end of the cap, but not the rod.
Figure 4:
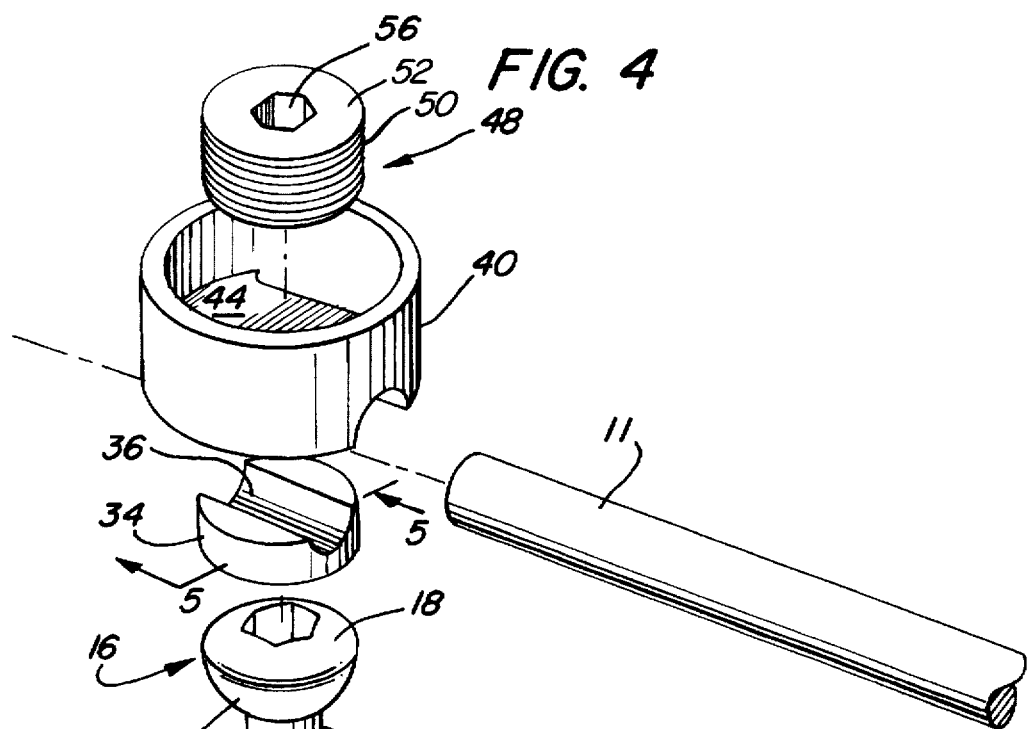
FIG. 4 is an exploded view of the screw assembly and rod.
Figure 5:
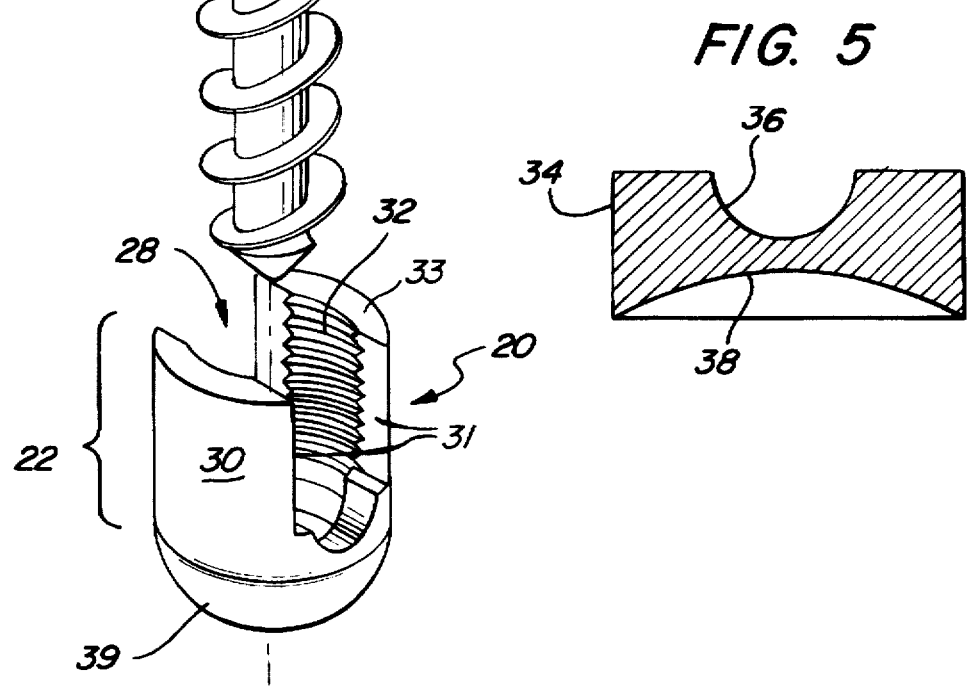
FIG. 5 is a cross-sectional view of the washer taken long lines 5—5 of FIG. 4.

As is illustrated in FIGS. 2 and 4, the screw assembly 10 includes a pedicle screw 12 which has a cylindrical shaft 14 threaded at 15, and a head 16 formed integrally with the shaft. The head of the screw has a generally convex semispherical bottom surface 17 extending upwardly from the shaft. The top of the head of the screw is of a generally convex semispherical shape 18 and includes an indentation in the form of a wrench engaging surface 19. The wrench engaging surface 19 is illustrated in the form of a hexagonal socket for receiving a suitable wrench such as an allen wrench. The wrench engaging surface could also be in the form of a slot for receiving a screwdriver or any other suitable recessed shape. The head of the screw has a diameter which is larger than the diameter of the threaded shaft 14 as is illustrated in FIG. 2.

A polyaxial housing 20 for receiving the screw, is composed of a top 22, a middle 24 and bottom section 26, as shown in FIG. 2. A stepped axial bore 28 extends through the housing with the bore in the top section 22 having a diameter larger than the diameter of the threaded shaft of the screw. The top section defines a pair of upstanding posts 30 with a rod receiving slot 31 therebetween. The inside walls 32 of the posts are threaded to receive a set screw, to be described. The middle section 24 of the housing defines an inner generally spherically concave surface 27 adapted to engage the convex semi-circular bottom surface 17 of the head of the screw.

The bore in the bottom section 26 of the housing has a diameter which is greater than the diameter of the threaded cylindrical shaft 14, but smaller than the diameter of the head 16 of the screw. When assembled the screw is placed within the polyaxial housing 20 such that the bottom 17 of the head of the screw 12 comes into contact with the spherically concave portion of the middle section 27, as is illustrated in FIG. 2. The top section 22 of the housing as a cylindrical outer surface 33, interrupted by the slot 31 and the middle and bottom sections have a generally spherical exterior surface 39 which extends from the upper surface 33 to the bore 28.

A washer 34 is adapted to be placed between the rod and the upper surface of the head of the screw as is illustrated in FIGS. 2 and 4. The top surface of the washer 34 includes a generally concave longitudinal surface 36 which receives the rod 11. The bottom surface of the washer is generally spherically concave in shape for engaging the top surface 18 of the head of the screw 12.

A cup-shaped cap 40, having a cylindrical outer and inner surface 41 and 42, is adapted to be placed over the polyaxial housing 20 and engage the top of the rod 11, as is illustrated in FIGS. 2 and 4. The cap 40 has a bottom with a pair of spaced arcuate openings 43 for receiving the posts 30 and a cross-connector 44 spanning the lateral width of the lower inside surface of the cap between the openings. The cross-connector 44 has a top 46a that is flat and a bottom 46 that includes a longitudinal concave surface 47 (i.e., semicylindrical saddle or U-shaped surface) which engages the rod 11. The cap is adapted to be placed over the outside of the polyaxial housing so that the posts 30 extend through the openings 43 thus allowing the cross-connector to be received between the posts and within the slot 28 of the housing. The cup-shaped cap 40 is arranged to proceed downwardly within the axial bore of the polyaxial housing until the bottom of the cross-connector comes into contact with the rod 11.

A conventional set screw 48 completes the pedicle screw assembly. The set screw includes external threads 50, a top 52, and a bottom 58. The top 52 has a hexagonal indentation or recess which serves as a wrench engaging surface 56, i.e., a hexagonal socket. The bottom 58 is flat. When inserted into the axial bore of the polyaxial housing the threads of the set screw come into contact with the threads on the inner walls of the posts 30. As the set screw 48 is tightened, the bottom of the set screw 58 comes into contact with the top of the cross-connector 44 forcing the housing upwardly or the rod downwardly or both until the rod is firmly captured between the head of the implanted screw (including the washer) and the cap.

Since the set screw fits inside of the polyaxial housing, there is no contact between the set screw and the tissue of the patient. This reduces the risk of tissue damage and allows for a more limited area of surgical intrusion for the installation of the pedicle screw assembly. Further, the wrench engaging surface is more accessible and requires a less bulky wrench or securing device to accomplish the tightening process. These factors lessen the time required for the operation, minimize tissue damage, and utilizes a smaller securing device to fix the assembly into position.

Before the final tightening operation, the polyaxial housing is freely rotatable and angularly displaceable about the head of the implanted screw. This freedom of movement, to accommodate any bends in the rod, is referred to herein as three degrees of freedom. As the proper alignment is achieved, the assembly can be secured in a single desired position by the final tightening of the set screw.

As a result of this procedure, the bone segments are brought into a stable immobilized position. This is best understood by referring to FIG. 1. This figure shows the pedicle assembly and rod in place for the immobilization of spinal bone segments. The rod is connected to other pedicle screw assemblies, not shown, and thus keeps the bone segments in an immobilized state.

The components of the screw assembly as well as the rod may be made of a high strength material, such as stainless steel, or preferably titanium, which is compatible with the surrounding bone and tissue.

The parameters of the present device may be altered in numerous ways without departing from the spirit and scope of the invention as defined in the appended claims. Therefore, it is intended that the drawing be interpreted as illustrative and not in any way viewed as being a limitation on the invention.

What is claimed is:

1. A pedicle screw assembly for use in conjunction with a rod for immobilizing bone segments comprising:

a screw having a cylindrical threaded shaft and a head, the head having a larger diameter than the shaft with a generally spherically convex bottom section jointed to the shaft and a top section defining a wrench engaging surface so that the screw may be rotatably inserted into a bone segment;

a polyaxial housing having a top, middle and bottom section, with a stepped axial bore therethrough, the diameter of the bore in the bottom section being larger than the diameter of the cylindrical shaft and smaller than the diameter of the screw head, the diameter of the bore in the top section of the housing having a diameter greater than the diameter of the head of the screw, the middle section of the housing having a generally spherically concave inside surface extending between the bore diameters in the top and bottom sections whereby the cylindrical shaft of the screw may pass through the housing while the head is retained in the middle section of the housing, the top section of the housing defining a pair of spaced upstanding posts with a threaded inside surface, the posts defining a slot therebetween for receiving the rod;

a cup-shaped cap adapted to be inserted over the top section of the housing after the rod has been inserted through the housing slot, the cap having a bottom defining a pair of spaced openings for receiving the posts and a cross-connector spanning the lateral width of the inside surface of the cap between the openings, the cross-connector having a lower concave surface for engaging the rod and an upper surface;

a set screw having a head with a wrench engaging surface, a threaded shaft adapted to be threadably received in the threaded surface of the housing and a free end for engaging the upper surface of the cross-connector of the cap to secure the rod between the cross-connector and the screw head; and a washer with a top and bottom, the bottom of the washer including a concave surface adapted to engage the head of the screw, the top of the washer having a concave recess adapted to engage the rod, the washer being located within the polyaxial housing between the head of the screw and the rod.

2. The pedicle screw assembly of claim 1 wherein the screw, housing, cap, and set screw are made of titanium.

3. A pedicle screw assembly for use in conjunction with a rod for immobilizing bone segments comprising:

a screw having a cylindrical threaded shaft and a head having a larger diameter than the shaft with a generally spherically convex bottom section jointed to the shaft and a top section having a generally spherical convex surface defining a wrench engaging surface therein so that the screw may be rotatably inserted into a bone segment;

a polyaxial housing having a top, middle and bottom section, with a stepped axial bore therethrough, the diameter of the bore in the bottom section being larger than the diameter of the cylindrical shaft and smaller than the diameter of the screw head, the diameter of the bore in the top section of the housing having a diameter greater than the diameter of the head of the screw, the middle section of the housing having a generally spherically concave inside surface extending between the bore diameters in the top and bottom sections whereby the cylindrical shaft of the screw may pass through the housing while the head is retained in the middle section of the housing, the top section of the housing defining a pair of spaced upstanding posts with a threaded inside surface, the posts defining a slot therebetween for receiving the rod;

a washer adapted to be inserted into the polyaxial housing after insertion of the screw through the polyaxial housing, the washer having a top and bottom, the bottom of the washer having a generally concave spherical shape being adapted to receive the head of the screw, the rod being inserted through the housing slot coming into contact with the top of the washer, the top of the washer having a longitudinal saddle shaped recess being adapted to receive the rod;

a cup-shaped cap adapted to be inserted over the top section of the housing after the washer is in place between the head of the screw and the rod, the cap having a bottom defining a pair of spaced openings for receiving the posts and a cross-connector spanning the lateral width of the inside surface of the cap between the openings, the cross-connector having a lower generally cylindrical concave surface for engaging the rod and an upper surface; and a set screw having a head with a wrench engaging surface, a threaded shaft adapted to be threadably received in the threaded surface of the housing and a free end for engaging the upper surface of the cross-connector of the cap to secure the rod between the cross-connector and the screw head.

4. A pedicle screw assembly for use in conjunction with a rod for immobilizing bone segments comprising:

- a screw having a threaded shaft and a heads the head having a larger diameter than the shaft and defining a generally spherically convex bottom and top surface and a wrench engaging socket in the top surface;
- a polyaxial housing having a top, middle and bottom section, with a stepped axial bore therethrough, the diameter of the bore in the bottom section being larger than the diameter of the threaded shaft of the screw and smaller than the diameter of the screw head, the diameter of the bore in the top section of the housing having a diameter greater than the diameter of the head of the screw, the middle section of the housing defining a generally spherically concave interior surface extending between the bore diameters in the top and bottom sections whereby the cylindrical shaft of the screw may pass through the housing while the head is retained in the middle section of the housing, the top section of the housing defining at least two spaced upstanding posts with a threaded inside surface, and a slot therebetween for receiving the rod, the housing being arranged to pivot and rotate relative to the head of the screw to accommodate bends in the rod;
- a cup-shaped cap adapted to be inserted over the top section of the housing after the rod has been inserted through the housing slot, the cap having a bottom defining at least two spaced openings for receiving the posts and a cross-connector spanning the lateral width of the inside surface of the cap between the openings, the cross-connector having a lower generally semi-cylindrical concave surface for engaging the rod and an upper surface;
- a set screw having a head with a wrench engaging surface, a threaded shaft adapted to be threadably received in the threaded surface of the upper section housing and a free end for engaging the upper surface of the cross-connector of the cap to secure the rod between the cross-connector and the screw head so that the rod is held in a fixed position relative to the head of the screw, and
- a washer disposed between the cross-connector of the cap and the head of the screw, the washer having a generally concave spherical lower surface and a saddle-shaped upper surface.

5. A pedicle screw assembly for use in conjunction with a rod for immobilizing bone segments comprising:

- a screw having a cylindrical threaded shaft and a head having a larger diameter than the shaft with a generally spherically convex bottom section joined to the shaft and a top section defining a wrench engaging surface so that the screw may be rotatably inserted into a bone segment;
- a polyaxial housing having an upper and a lower section with an axial passageway therethrough, the passageway in the lower section being larger than the diameter of the threaded shaft of the screw and smaller than the diameter of the screw head, the passageway in the upper section of the housing being larger than the diameter of the head of the screw, whereby the cylindrical shaft of the screw may pass through the housing while the head is retained within the housing, the upper section of the housing defining at least two spaced arcuate upstanding posts with a threaded inside surface, the posts defining a slot therebetween for receiving the rod;
- a cup-shaped cap adapted to be inserted over the top section of the housing, the cap having a bottom defining spaced openings for receiving the posts and a cross-connector having a lower surface adapted to engage the rod;
- means for threadably engaging the inside surface of the upstanding posts to capture the rod between the housing and the head of the screw; and
- a washer positioned between the head of the screw and the rod, the washer having a lower generally concave spherical surface for engaging the screw head and an upper U-shaped surface for engaging the rod.

* * * * *

UNITED STATES PATENT AND TRADEMARK OFFICE
CERTIFICATE OF CORRECTION

PATENT NO. : 5,782,833
DATED      : July 21, 1998
INVENTOR(S) : Thomas T. Haider It is certified that error appears in the above-indentified patent and that said Letters Patent is hereby corrected as shown below:

In the Abstract, line 6, "18" should read --12--.

Column 4, line 27, "as" should read --has--.

Column 7, line 3, "heads" should read --head,--.

Signed and Sealed this

Twenty-ninth Day of September, 1998

Attest:

BRUCE LEHMAN

*Attesting Officer*    *Commissioner of Patents and Trademarks*